United States Patent [19]

Gellatly et al.

[11] Patent Number: 4,769,365
[45] Date of Patent: Sep. 6, 1988

[54] CERTAIN CARBOXYLIC AZETIDINE DERIVATIVES USEFUL IN REDUCING BLOOD CHOLESTEROL

[75] Inventors: James B. M. Gellatly, Canterbury; John G. Martin, Sittingbourne, both of England

[73] Assignee: Shell Oil Company, Houston, Tex.

[21] Appl. No.: 937,287

[22] Filed: Dec. 3, 1986

Related U.S. Application Data

[63] Continuation-in-part of Ser. No. 870,220, Jun. 3, 1986, abandoned.

[30] Foreign Application Priority Data

Jun. 4, 1985 [GB] United Kingdom ................. 8514075

[51] Int. Cl.$^4$ ..................... A61K 31/40; C07D 00/00
[52] U.S. Cl. .................................... 514/210; 548/953
[58] Field of Search ......................... 548/953; 514/210

[56] References Cited

U.S. PATENT DOCUMENTS 4,555,260 11/1985 Devlin ..................................... 71/88
4,560,401 12/1985 Devlin ..................................... 71/88

FOREIGN PATENT DOCUMENTS 29265 6/1981 European Pat. Off. .

Primary Examiner—Donald G. Daus
Assistant Examiner—William A. Teoli, Jr.

[57] ABSTRACT

Compound for use in a method for treatment of the human or animal body by therapy, characterized in that the compound is a carboxy azetidine derivative of the general formula I or a pharmaceutically acceptable salt, ester, amide, alkylamide, hydrazide or alkylhydrazide thereof:

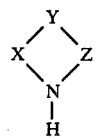

in which:
X represents one of the groups $CH_2$, CHR or $CR_2$.
Y represents one of the groups $CH_2$, CHR, $CR_2$ or $CH.CO_2H$ and
Z represents one of the groups $CH_2$, CHR, $CR_2$ or $CH.CO_2H$;
the or each R independently represents an alkyl, alkenyl or cycloalkyl group or an aryl or aralkyl group optionally substituted on the aryl nucleus by one or more of the same or different substituents selected from halogen atoms, alkyl groups and alkoxy groups; and one but only one of Y and Z must represent a $CH.CO_2H$ group.

6 Claims, No Drawings

CERTAIN CARBOXYLIC AZETIDINE DERIVATIVES USEFUL IN REDUCING BLOOD CHOLESTEROL

This application is a continuation-in-part of application Ser. No. 870,220, filed on June 3, 1986 now abandoned.

The present invention relates to the therapeutic use of certain carboxylic azetidine derivatives, in particular their use in reducing the level of cholesterol in blood. European Patent No. 0029265 describes the production of plants in which male sterility has been brought about by treatment with certain carboxy azetidine derivatives. It has now been unexpectedly found that this type of compound also exerts a therapeutic effect in mammals, in particular by reducing the level of cholesterol in blood. Cardiovascular diseases, for example ischemic heart diseases, atherosclerosis and hypertension are amongst the more commonly occurring causes of death. These are often caused by insufficient blood flow resulting from atherosclerosis, which is generally associated with elevated levels of blood serum cholesterol. Compounds which reduce the cholesterol level in blood therefore offer a valuable therapeutic tool in reducing the risk of cardiovascular disease.

The present invention therefore provides a compound for use in a method for treatment of the human or animal body by therapy, particularly by reducing blood cholesterol levels, characterised in that the compound is a carboxy azetidine derivative of the general formula I or a pharmaceutically acceptable salt, ester, amide, alkylamide, hydrazide or alkylhydrazide thereof:

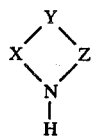

I in which:

X represents one of the groups $CH_2$, CHR or $CR_2$;

Y represents one of the groups CHR, $CR_2$ or $CH.CO_2H$ and

Z represents one of the groups $CH_2$, CHR, $CR_2$ or $CH.CO_2H$;

the or each R independently represents an alkyl, alkenyl or cycloalkyl group or an aryl or aralkyl group optionally substituted on the aryl nucleus by one or more of the same or different substituents selected from halogen atoms, alkyl groups and alkoxy groups;

and one but only one of Y and Z must represent a $CH.CO_2H$ group.

It also has been found that Y can represent a $CH_2$ group.

Preferably the or each R independently represents an alkyl or alkenyl group having up to 6, especially up to 4, carbon atoms, a cycloalkyl group having from 3 to 6 carbon atoms, or a phenyl or benzyl group optionally substituted by one or more, preferably one or two, of the same or different substituents selected from chlorine, fluorine or bromine atoms, alkyl groups having from 1 to 4 carbon atoms and alkoxy groups having 1 to 4 carbon atoms.

More preferably the or each R independently represents a methyl or ethyl group or a phenyl group optionally substituted by one or two substituents selected from fluorine and chlorine atoms and methyl and methoxy groups.

Preferably X represents $CH_2$ or CH(alkyl), Y represents $CH_2$, CH(alkyl) or $CH.CO_2H$ and Z represents $CH_2$ or $CH.CO_2H$, one of Y and Z being $CH.CO_2H$.

The azetidine derivative may for example be the free acid of the general formula I; a hydrohalide or an alkali metal salt thereof; the amide or hydrazide thereof in which the amide or hydrazide group may be substituted by one or two alkyl, preferably C(1-4) alkyl, especially methyl, groups; an alkyl, alkenyl or aralkyl ester, preferably an alkyl or alkenyl ester having up to 10, especially up to 7, carbon atoms in the alkyl or alkenyl group; or a hydrohalide of such an amide, hydrazide or ester.

Preferably the azetidine derivative is the free acid of formula I, a hydrohalide or an alkali metal salt thereof, the hydrazide thereof, a C(1-10) alkyl ester thereof or a hydrohalide of said hydrazide or ester. Especially preferred is the free acid of formula I or a C(1-4)alkyl ester, for example the methyl ester, thereof, or a hydrohalide of said acid or ester.

Especially preferred azetidine derivatives are 3-carboxyazetidine, its methyl ester hydrochloride, 2-carboxy-3-methylazetidine, 2-carboxy-4-methylazetidine and 3-carboxy-2-methylazetidine.

The azetidine derivative may exist in the form of isomers depending on the meaning of the group X, Y and Z. For example, 2-carboxy-3-methylazetidine exists as geometric isomers depending on the relative positions of the carboxy and the methyl group, and in addition, for each of these geometric isomers, optical isomers exist. As is usual in processes involving biological systems, some isomers may be more therapeutically active than others.

Administration of the azetidine compounds for therapeutic use can be via any of the accepted modes of administration for therapeutic agents. These methods include oral, parenteral, transdermal, subcutaneous and other systemic modes. In order to facilitate administration, the azetidine compounds are suitably formulated in accordance with standard pharmaceutical practice as therapeutic compositions. Accordingly, the invention includes also a therapeutic composition which comprises a carboxy azetidine derivative of the general formula I as defined above in association with a carrier in a pharmaceutically acceptable level of purity. When the intended route of administration is parenteral, the therapeutic composition should, of course, be in a sterile form.

Depending on the intended mode, the compositions may be in the form of solid, semi-solid or liquid dosage forms, such as, for example, tablets, pessaries, suppositories, pills, capsules, powders, liquids, suspensions, or the like, preferably in unit dosage forms suitable for single administration of precise dosages. The compositions, whether or not in unit dosage form, can conveniently be in the form of a pack which comprises such a composition, together with instructions for use in a method of treatment by therapy. The compositions will include a conventional pharmaceutical excipient and an active compound of formula I or the pharmaceutically acceptable salts thereof and, in addition, may include other medicinal agents, pharmaceutical agents, carriers adjuvants, diluents, etc.

For solid compositions, conventional non-toxic solid include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administerable compositions can, for example, be prepared by dissolving, dispersing, etc. an active compound as defined above and optional pharmaceutical adjuvants in an excipient, such as, for example, water, saline, aqueous dextrose, glycerol, ethanol, and the like, thereby forming a solution or suspension. If desired, the pharmaceutical composition to be administered may also contain minor amounts of nontoxic auxiliary substances such as wetting agents, pH buffering agents and the like, for example, sodium acetate, sodium lauryl sulphate, sorbitan monolaurate, triethanolamine sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain as quantity of the active compound(s), a therapeutically effective amount, i.e. in an amount effective to achieve cholesterol reduction in the subject being treated.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 10%–95% active ingredient, preferably 1–70%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795.

The dosage employed is preferably in the range of 0.1 to 200 mg active ingredient per day per kg body weight. As indicated above, the therapeutic effect of particular interest is the reduction of cholesterol levels in blood. In order to achieve this effect, the dosage of azetidine compound administered should normally be at least 100 ppm of subject diet, (corresponding approximately to 10–20 mg active compound per day per kg body weight) with the upper limit being determined by other factors such as economics and avoidance of undesired side-effects, It is also believed that other therapeutic effects may occur, particularly on tissues. For example, rat studies indicate that mortality over a two-year period is reduced, apparently because treated rats suffer less from chronic renal disease than control rats.

The invention is illustrated in the following Examples.

EXAMPLE 1

Rats (Fischer 344 strain) were fed a standard diet (LAD 2, supplied by K. & K. Greff Chemicals Ltd., Croydon, England) to which had been added varying amounts of test compound. The trial used 75 male and 75 female rats, with 15 of each sex in each dose group. Blood samples taken by retro-orbitol bleeding after the animlas had been fed for 13, 26 and 52 weeks, and the concentration of cholesterol in the blood plasma determined by a standard enzymatic colorimetric test, kinetically measured (ref. Siedel, J. et al (1981). J. Clin. Chem. Clin. Biochem. 19,838). The test compound was azetidine-3-carboxylic acid, and the results are set out in Table 1 below.

Subsequently, retroorbital blood samples were obtained at week 78 and cardiac blood samples at termination of this 2 year study; data obtained confirm the trends of Table 1. Survival of male rats to study termination was substantially greater in the 1000 ppm group (64% survival) than in the controls or intermediate groups (24–48%). Preliminary observations at necropsy suggest that deaths due to chronic renal disease were fewer in the 1000 ppm group than in the other groups.

TABLE 1

| Concn. Test Compound | 0 (Control) | Concentration of cholesterol (M Mole/liter) | | | |
| --- | --- | --- | --- | --- | --- |
| | | 3.0 ppm diet | 30 ppm diet | 100 ppm diet | 1000 ppm diet |
| Males at 13 weeks | 2.3 | 2.2 | 2.2 | 2.1** | 1.9** |
| Females at 13 weeks | 3.0 | 3.0 | 2.8 | 2.5** | 2.0** |
| Males at 26 weeks | 2.11 | 2.09 | 1.80* | 1.66** | 1.21** |
| Females at 26 weeks | 3.29 | 3.15 | 2.56** | 2.17** | 1.41** |
| Males at 52 weeks | 2.52 | 2.55 | 2.14 | 2.17** | 1.41 |
| Females at 52 weeks | 2.57 | 3.54 | 2.95 | 2.50 | 1.53 |

Single and double stars indicate 95 and 99% levels of significant differences, respectively, from controls. (The data for 52 weeks have not been analysed statistically, so no stars are assigned.) In both sexes and at all times there was a reduction in the concentration of plasma cholesterol at 100 and 1000 ppm in the diet of azetidine-3-carboxylic acid (corresponding, respectively to approximately 10 and 100 mg/kg/day).

EXAMPLE 2

Mice (C57/C3H hybrid) were fed for 13 weeks on a standard laboratory diet (LAD 2, supplied by K. & K. Greff Chemicals Ltd., Croydon, England) to which had been added varying amounts of test compound. The trial used 75 male and 75 female mice, with 15 of each sex in each dose group. Blood samples were taken by retro-orbital bleeding, and the concentration of cholesterol in the blood plasma determined by the standard enzymatic colorimetric test (as used for Ex. 1). The test compound was azetidine-3-carboyxlic acid, and the results are set out in Table 2 below.

TABLE 2

| Concn. Test Compound | Concentration of cholesterol (M Mole/liter) | | | | |
|---|---|---|---|---|---|
| | 0 (Control) | 3.0 ppm diet | 30 ppm diet | 100 ppm diet | 1000 ppm diet |
| Males | 3.15 | 3.30 | 3.03 | 3.71 | 2.78 |
| Females | 2.76 | 2.78 | 2.63 | 2.37 | 2.22 |

In both the males and the females, the concentration of cholesterol was less in the group fed 1000 ppm (corresponding approximately to 200 mg/kg/day) of test compound than it was in the control group.

EXAMPLE 3

Groups of 7 male and 7 female Fischer 344 rats were fed for 5 weeks on standard laboratory diet (LAD 2) containing 2500 ppm azetidine-3-carboxylic acid or 2500 ppm of the methyl ester hydrochloride of azetidine-3-carboxylic acid. A group of 21 males and 21 females were fed LAD 2 only (controls). Cardiac blood samples were obtained at terminal necropsy and the concentrations of plasma cholesterol determined as in Example 1.

Results indicate that the concentrations of plasma cholesterol were less (reductions in males 13–15%; reductions in females 35–40%) in the groups fed azetidine-3-carboxylic acid and the methyl ester hydrochloride of azetidine-3-carboxylic acid than in the controls.

EXAMPLE 4

Groups of 3 male and 3 female hyperlipidaemic homozygotic rabbits (Froxfield) were fed standard rabbit diet containing 0 (controls) or 2500 ppm azetidine-3-carboxylic acid for eight weeks. Blood samples were obtained prior to initiation of the study (day 0), at day 28 and at termination (day 56) for estimation of local plasma cholesterol (method of Roeschau et al. (1974) Klin Chem., V Klin Biochem., 12, 226). Results are presented in Table 3, and show a marked reduction of plasma cholesterol in the treated animals over the period of the study.

TABLE 3

| Treatment/Sex | Plasma cholesterol (m mol $1^{-1}$) | | |
|---|---|---|---|
| | Day 0 | Day 28 | Day 56 |
| CONTROL | | | |
| Males | 20.3 | 18.3 | 17.6 |
| Females | 16.7 | 19.1 | 22.3 |
| AZETIDINE-3-CARBOXYLIC ACID | | | |
| Males | 22.4 | 16.1 | 16.7 |
| Females | 24.5 | 16.7 | 13.2* |

*One female killed on day 46 due to illness; mean presented is for two survivors only.

EXAMPLE 5

Pharmaceutical compositions

The following examples illustrate pharmaceutical compositions according to the invention. In the examples, the active ingredient is either 3-carboxyazetidine or its methyl ester hydrochloride. Other azetidine derivatives may be formulated in a similar manner.

Tablet for oral administration

| | mg/tablet |
|---|---|
| Active ingredient | 250 |
| Sodium starch glycollate | 5 |
| Microcrystalline cellulose | 45 |
| Sodium lauryl sulphate | 3 |

The active ingredient and the microcrystalline cellulose are sieved through a 40 mesh screen. The sodium starch glycollate and sodium lauryl sulphate are sieved through a 60 mesh screen. The powders are blended together in a suitable blender until homogeneous. The mixture is then compressed on appropriate punches on an automatic tablet machine. The tablets may be covered in a thin polymer coat applied by the usual film coating technique. A pigment may be included in the film coat.

Capsule for oral administration

| | mg/capsule | mg/capsule |
|---|---|---|
| Active ingredient | 200 mg | 2.5 |
| *Starch | 150 mg | 97.0 |
| magnesium stearate | 5.0 mg | 1.0 |

*a form of directly compressible starch

The active ingredient is sieved and blended with the excipients. The mix is then filled into hard gelatine capsules using suitable machinary. Other doses may be prepared by altering the fill weight.

EXAMPLE 6

In further tests, 4-methylazetidine-2-carboxylic acid, 3-methylazetidine-2-carboxylic acid and 2-methylazetidine-3-carboxylic acid, hereinafter designated as Compounds A, B and C, respectively, were tested as follows: Rats (Fisher 344 strain) were fed standard diet LAD 2 to which had been added 2500 ppm of test compound. The trial used seven rats of each sex for each chemical. Blood samples were taken by cardiac bleeding after the animals had been fed for five weeks, and the concentration of cholesterol in the blood plasma determined by the colorimetric test described in Example 1.

The results are set forth in Table 4.

TABLE 4

| Compound | Concentration of cholesterol (mmol/liter) | | Percent reduction in cholesterol, compared to control | |
|---|---|---|---|---|
| | Male rats | Female rats | Male rats | Female rats |
| None (control) | 1.53 | 2.06 | — | — |
| A | 1.28 | 1.94 | 16 | 6 |
| B | 1.17 | 1.87 | 24 | 9 |
| C | 1.46 | 1.95 | 4 | 5 |

We claim:

1. A method for treatment of an animal by therapy that comprises administering to an animal in need of therapy to reduce blood cholesterol levels a therapeutically effective dosage of a carboxyazetidine of formula I or a pharmaceutically acceptable salt, ester, amide, alkylamide, hydrazide or alkylhydrazine thereof:

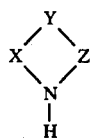 (I)

in which:
X represents one of the groups $CH_2$, CHR or $CR_2$;
Y represents one of the groups $CH_2$, CHR, $CR_2$, or $CH.CO_2H$;
Z represents one of the groups $CH_2$, CHR, $CR_2$ or $CH.CO_2H$;
R independently represents an alkyl or alkenyl group having up to 6 carbon atoms, a cycloalkyl group having from 3 to 6 carbon atoms, or a phenyl or benzyl group optionally substituted on the nucleus by one or more of the same or different substituents selected from chlorine, fluorine or bromine atoms, alkyl groups having from 1 to 4 carbon atoms, and alkoxy groups having 1 to 4 carbon atoms; and one but only one of Y and Z must represent a $CH.CO_2H$ group.

2. A method as claimed in claim 1 wherein the or each R independently represents an alkyl or alkenyl group having from 3 to 6 carbon atoms, or a phenyl or benzyl group optionally substituted by one or more of the same or different substituents selected from chlorine, fluorine or bromine atoms, alkyl groups having from 1 to 4 carbon atoms and alkoxy groups having 1 to 4 carbon atoms.

3. A method as claimed in claim 1 wherein the or each R independently represents a methyl or ethyl group or a phenyl group optionally substituted by one or two substituents selected from fluorine and chlorine atoms and methyl and methoxy groups.

4. A method as claimed in claim 3 wherein the carboxyazetidine is in the form of the free acid, a C(1–4)alkyl ester thereof, or a hydrohalide of said acid or ester.

5. A method as claimed in claim 4 wherein each R represents an alkyl moiety.

6. A method according to claim 5 wherein the active compound is 3-carboxyazetidine.

* * * * *